United States Patent [19]
Arenas

[11] Patent Number: 5,640,970
[45] Date of Patent: Jun. 24, 1997

[54] GUIDEWIRE HAVING A CONTROLLED RADIOPACITY TIP

[75] Inventor: Alvaro Arenas, deceased, late of Miami, Fla., by Patricia Arenas, heir

[73] Assignee: Cordis Corporation, Miami Lakes, Fla.

[21] Appl. No.: 427,877

[22] Filed: Apr. 26, 1995

[51] Int. Cl.$^6$ .................................................... A61B 5/00
[52] U.S. Cl. .................................................... 128/772
[58] Field of Search .................................. 128/657, 772; 604/95, 280–283

[56] References Cited

U.S. PATENT DOCUMENTS

| | | | |
|---|---|---|---|
| 4,922,924 | 5/1990 | Gambale et al. | 128/772 |
| 5,063,935 | 11/1991 | Gambale | 128/772 |
| 5,174,302 | 12/1992 | Palmer | 128/772 |
| 5,345,945 | 9/1994 | Hodgsen et al. | 128/772 |
| 5,353,808 | 10/1994 | Viera | 128/772 |
| 5,363,847 | 11/1994 | Viera | 128/772 |
| 5,460,187 | 10/1995 | Daigle et al. | 128/772 |

Primary Examiner—Max Hindenburg
Attorney, Agent, or Firm—Thomas R. Vigil

[57] ABSTRACT

The controlled radiopaque guidewire comprises: an elongate central core wire having a reduced in diameter distal end portion; a rounded tip member having a back side to which is connected a distal end of the core wire; a first coiled spring wire having a proximal end fixed to the core wire in a proximal area thereof and a distal end fixed to the back side of the tip member; the coils of the first coiled spring wire being stretched or spaced in a distal end portion thereof; a second coiled spring wire having a proximal end fixed to the core wire and coiling outward therefrom to and between the spaced apart coils in the first coiled spring wire in the distal end portion of the first coiled spring wire and interleaved therebetween; a distal end of the second coiled spring wire being fixed to the back side of the tip member; the proximal end of the second coiled spring wire being spaced inwardly of and not in connection with coils of the first coiled spring wire; and the second coiled spring wire being more radiopaque than the first coiled spring wire.

5 Claims, 3 Drawing Sheets

5,640,970

GUIDEWIRE HAVING A CONTROLLED RADIOPACITY TIP

BACKGROUND OF THE INVENTION

1. Field of the Invention.

The present invention relates to a guidewire having a controlled radiopacity tip. More specifically the present invention relates to a guidewire having a central core wire with a tapered end fixed at its distal end to a rounded tip and a coiled spring wire having its outer distal end also connected to the rounded tip. The coiled spring wire is a non-radiopaque coiled wire and a second radiopaque coiled spring wire is fixed at a proximal end to the center core wire near the beginning of the taper thereof and at a distal end to the rounded tip. The radiopaque coil is interwound or interleaved with the outer non-radiopaque coil and also fixed to the rounded tip. Preferably the spacing between the interleaved radiopaque coils and non-radiopaque coils increases from the beginning of the interleaving to the rounded tip.

2. Description of the related art including information disclosed under 37 CFR §§1.97–1.99.

Heretofore, coiled spring guidewires have been proposed having varying radiopacity and having varying spacing or varying pitch in the coils at the distal end thereof to provide more flexibility in the distal end portion of the guidewire. Examples of some of these previously proposed guidewires are disclosed in the following U.S. Pat. Nos.:

| U.S. Pat. No. | Patentee |
|---|---|
| 4,721,117 | Mar et al. |
| 4,748,986 | Morrison et al. |
| 4,763,647 | Gambale |
| 4,813,434 | Buchbinder et al. |
| 4,846,186 | Box et al. |
| 4,922,924 | Gambale et al. |
| 5,063,935 | Gambale |
| 5,144,959 | Gambale et al. |
| 5,147,317 | Shank et al. |
| 5,174,302 | Palmer |
| 5,178,158 | de Toledo |
| 5,253,653 | Daigle et al. |
| 5,259,393 | Corso, Jr. et al. |

The Mar et al. U.S. Pat. No. 4,721,117 discloses a guidewire with flexibility and ease of shaping.

The Morrison et al. U.S. Pat. No. 4,748,986 discloses a coiled spring floppy guide wire with opaque tip. The coils in the distal end portion of the guidewire are highly opaque and stretched or spaced to provide flexibility.

The Gambale U.S. Pat. No. 4,763,647 discloses a steerable guidewire which provides for a change in the radiopacity of the distal portion of the guidewire to provide a more radiopaque segment at the distal portion than at more proximal portions. Gradual selected transitions of stiffness of the guidewire are achieved by varying the spacing of the individual turns of an outer coil and an inner coil surrounding a core wire at the distal end portion of the guidewire.

The Buchbinder et al. U.S. Pat. No. 4,813,434 teaches a steerable guidewire with a deflectable tip that is made deflectable by providing stretched coils in the distal end portion of the guidewire.

The Box et al. U.S. Pat. No. 4,846,186 discloses a coiled spring guidewire. The coils of a coiled spring wire of the guidewire are less tightly packed in the distal end portion of the guidewire to define gaps or spaces.

The Gambale et al. U.S. Pat. No. 4,922,924 teaches a guidewire having segments of varying radiopacity. For this purpose the guidewire includes a coil at the distal end which is formed from a highly radiopaque coil and a non-radiopaque coil arranged in bifilar arrangement to define a moderate radiopacity section in which the radiopaque and non-radiopaque segments alternate.

The Gambale U.S. Pat. No. 5,063,935 discloses a guidewire with varying radiopacity. The guidewire includes an outer small diameter highly radiopaque coiled wire. An inner helical coil formed from a larger diameter highly radiopaque wire is disposed within the outer coil and is attached at its proximal end to the distal end of a core wire shaft and at its distal end to a rounded tip within the outer coil. This guidewire defines an arrangement which, when viewed fluoroscopically, has a highly radiopaque distal portion and a moderately radiopaque proximal portion.

The Gambale et al. U.S. Pat. No. 5,144,959 teaches a catheter guidewire with varying radiopacity similar to the guidewire disclosed in U.S. Pat. No. 5,063,935 with the exception that the distal end portion has regions of high radiopacity, moderate radiopacity and relatively no radiopacity.

The Shank et al. U.S. Pat. No. 5,147,317 teaches a varied radiopacity guidewire which has a distal tip which presents a relatively dark radiopaque image and proximal portions which present a less radiopaque, relatively gray, image.

The Palmer U.S. Pat. No. 5,174,302 teaches a guidewire with varied radiopacity and spaced, highly radiopaque regions which are established by banded portions that are highly radiopaque.

The de Toledo U.S. Pat. No. 5,178,158 teaches a convertible guidewire-catheter with a soft tip having spaced apart flat wire coils in a distal end thereof to render the distal end more flexible.

The Daigle et al. U.S. Pat. No. 5,253,653 discloses a fluoroscopically viewable guidewire for a catheter. The guidewire has a core wire disposed within a coiled spring wire and a linear array of radiopaque markers disposed on the core wire adjacent the distal tip of the guidewire.

The Corso, Jr. et al. U.S. Pat. No. 5,259,393 discloses a guidewire having a controlled radiopacity tip. The guidewire includes an outer loosely coiled proximal region which is less radiopaque and a tightly coiled distal region which is more radiopaque.

Also, a guidewire having spaced apart radiopaque marker bands on a core wire surrounded by a plastic sleeve is disclosed in U.S. application Ser. No. 07/942,777.

SUMMARY OF THE INVENTION

According to the present invention there is provided a controlled radiopaque guidewire comprising: an elongate central core wire having a reduced in diameter distal end portion; a rounded tip member having a back side to which is connected a distal end of the core wire; a first coiled spring wire having a proximal end fixed to the core wire in a proximal area thereof and a distal end fixed to the back side of the tip member; the coils of the first coiled spring wire being stretched or spaced in a distal end portion thereof; a second coiled spring wire having a proximal end fixed to the core wire and coiling outward therefrom to and between the spaced apart coils in the first coiled spring wire in the distal end portion of the first coiled spring wire and interleaved therebetween; a distal end of the second coiled spring wire being fixed to the back side of the tip member; the proximal

3 end of the second coiled spring wire being spaced inwardly of and not in connection with coils of the first coiled spring wire such that the coils in the proximal end portion of the second coiled spring wire have a smaller diameter than the coils of the first coiled spring wire; the second coiled spring wire being more radiopaque than the first coiled spring wire; the space in between the interleaved coils of the first and second coil spring wires increasing gradually from the beginning of the interleaving to the tip member and, at least one coil of the second coiled spring wire at the proximal end of the second coiled spring wire being wound tightly around a reduced in diameter portion of the central core wire and fixed to the central core wire and not being welded or otherwise fixed to coils of the first coiled spring wire.

DESCRIPTION OF THE PREFERRED EMBODIMENT(S)

Figure 1:
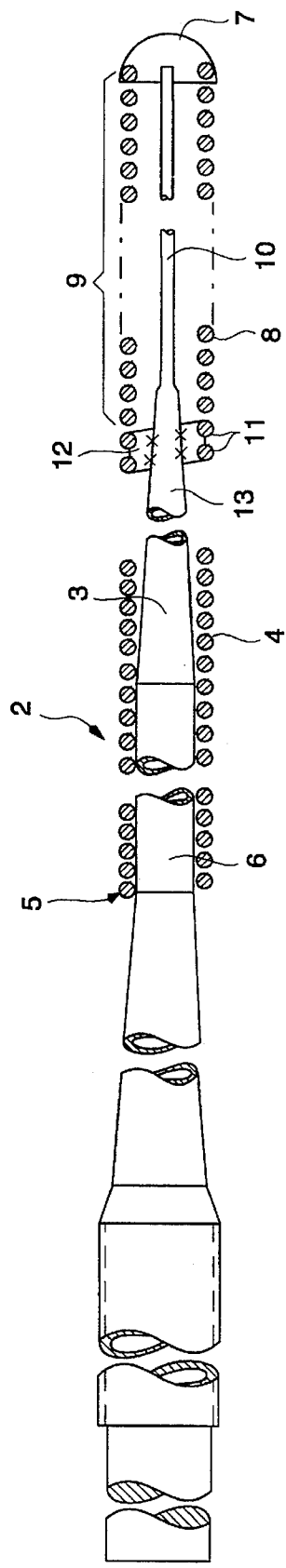
FIG. 1 is a longitudinal plan view, partly in section and with portions broken away, of a prior art guidewire.

Referring now to FIG. 1 there is disclosed therein a prior art guidewire 2 which includes a central core wire 3 having portions of different diameter and intermediate connecting tapered portions and a coiled spring wire 4 which is fixed at a proximal end 5 to a section 6 of one diameter of the central core wire 3 and extends distally to a distal tip member 7 to which it is fixed. The coils 8 in a distal end portion 9 of the coiled spring wire 4 are stretched or spaced apart to provide greater flexibility. Also, for greater flexibility the core wire 3 tapers to a distal small diameter rod or shaft 10 which extends to the tip member 7. As shown, several coils 11 of the coiled spring wire 4 are fixed, such as by a solder or brazed weld 12 to a tapered portion 13 of the core wire 3 just proximal to the distal rod 10 of the core wire 3, such that the coils 11 of the coiled spring wire are fixed to the core wire by the weld, or brazing or soldering 12. This guidewire 2 can be of the type disclosed in the Box et al. U.S. Pat. No. 4,846,186 or in the Palmer U.S. Pat. No. 5,174,302.

Figure 2:
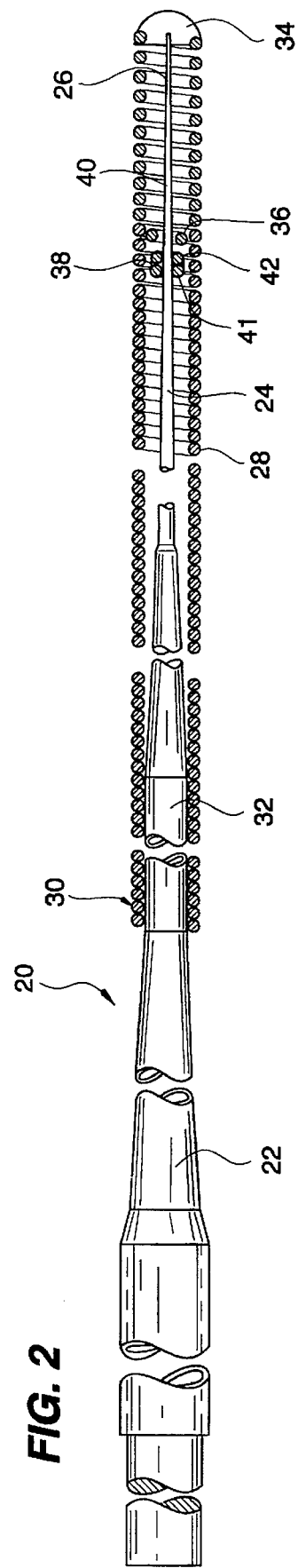
FIG. 2 is a longitudinal plan view, partly in section and with portions broken away, of a guidewire constructed according to the teachings of the present invention.

The guidewire 20 of the present invention is shown in FIG. 2 and includes a core wire 22 similar to the prior art core wire 3 except the core wire 22 has perhaps a longer distal rod or shaft 24 which tapers to a rod tip end 26. The guidewire 20 further includes a coiled spring wire 28 which is made of a highly non-radiopaque material and has a proximal end 30 that is fixed to a larger diameter portion 32 of the core wire 22 and extends distally to and is connected to a tip member 34 which can be a braised or soldered joint. The first coiled spring wire 28 can be made of a polymer or stainless steel which is highly non-radiopaque.

According to the teachings of the present invention, a second coiled spring wire 36 is fixed by a weld, or brazing or soldering at its proximal end 38 to the distal rod 24 of the core wire 22 near the beginning of the tapered area 40 of the distal rod 24 of the core wire 22 but is not welded or otherwise fixed to coils of the first coiled spring wire 28.

Figure 3:
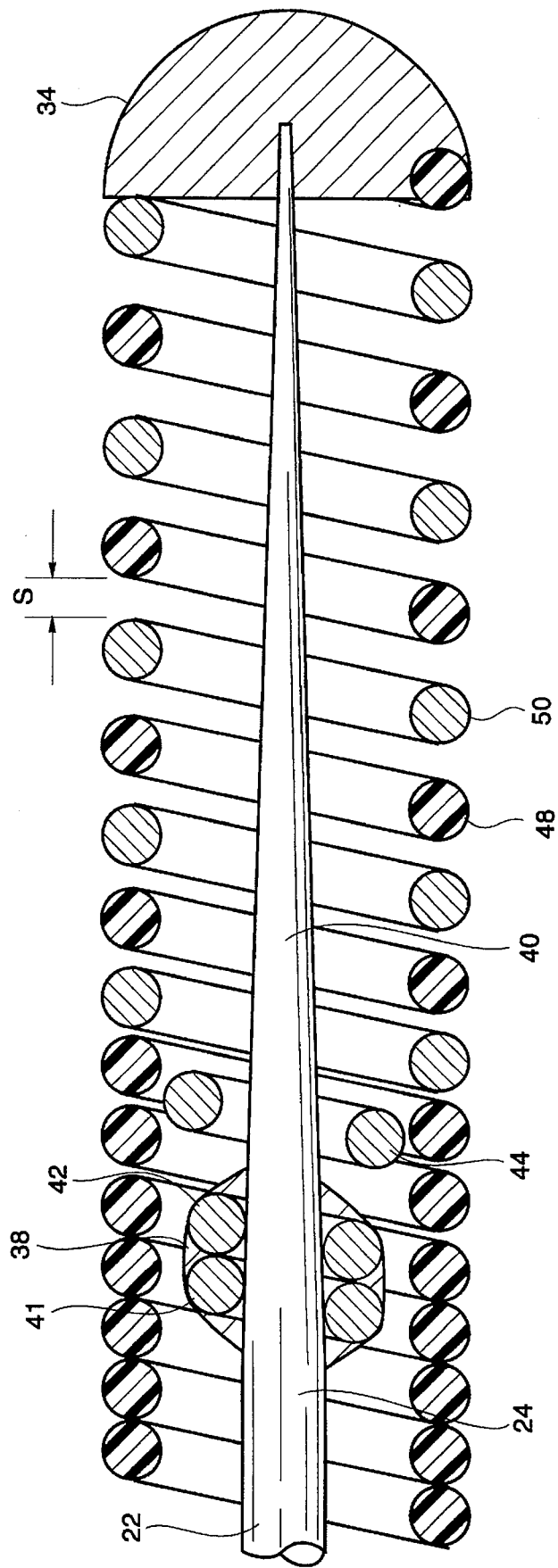
FIG. 3 is an enlarged sectional view of the distal end portion of the guidewire shown in FIG. 2 showing the connection of a proximal end of a radiopaque coil to a central core wire and the interleaving of coils of the radiopaque coil with coils of an outer less radiopaque coiled spring wire of the guidewire and showing variable spacing between the coils in a distal end portion of the guidewire.

As shown in FIGS. 2 and 3, two coils 41 and 42 at the proximal end 38 of the second coiled spring wire 36 are wound tightly around the distal rod 24 of the center core wire 22 and fixed thereto, such as by braising but again, not braised or welded or fixed to the surrounding coils of the first coiled spring wire 28. Then, the second coiled spring wire 36 extends from the proximal connection of the second coiled spring wire 36 to the distal rod 24 of the core wire 22 in at least one coil 44 within the coils 46 of the first coiled spring wire 28 to the first coiled spring wire 28 where coils 48 of the second coiled spring wire 36 are interwoven or interleaved with coils 50 of the first coiled spring wire 28. For this purpose, the coils 50 in a distal end portion 51 of the first coiled spring wire 28 are stretched or spaced apart to provide space for the interleaving of the coils 48 of the second coiled spring wire 36. The interleaved coils 48 and 50 extend to the tip member 34 where the distal end of each coiled spring wire 28 and 36 is fixed to the distal tip member 34 which can be a weld tip which is a braised or soldered weld.

According to the teachings of the present invention, the second coiled spring wire 36 is made of a highly radiopaque material so that it will be easily seen fluoroscopically when the guidewire is inserted into a vascular system.

Further according to the teachings of the present invention, the spacing(s) S between the interleaved coils 48 and 50 of the first and second coiled spring wires 28 and 36 gradually increases as the coils 48 and 50 approach the distal tip member 34 thereby to provide increased flexibility. Such increased flexibility is also provided by the tapering of the distal end portion of the rod 24 of the core wire 22.

Figures 4, 5:
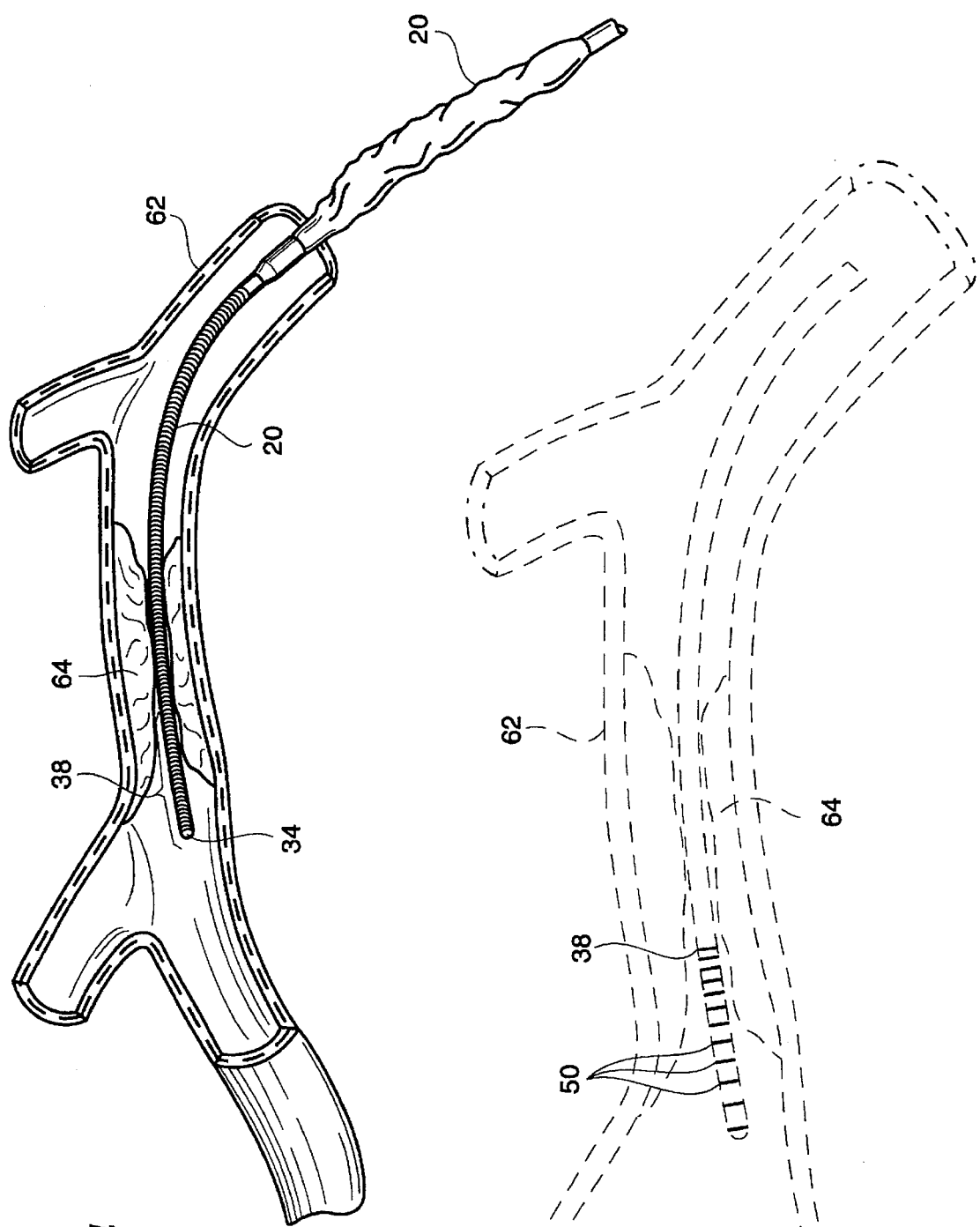
FIG. 4 is a plan view of the guidewire of the present invention mounted at the end of a balloon catheter and received within an occlusion in a blood vessel and with a portion of the blood vessel cut away to show the guidewire therein.
FIG. 5 is a plan view of the guidewire shown in FIG. 4 as it appears when viewed on a fluoroscopic examining screen, but with the spacing of the radiopaque coils exaggerated.

FIG. 5 shows the guidewire 20 of the present invention extending from a balloon catheter 60 and into a blood vessel 62 having a lesion or area of stenosis 64. A portion of the blood vessel 62 is cut away to better show the catheter 60 and area of stenosis 64.

FIG. 5 is a fluoroscopic view of the blood vessel 62 shown in FIG. 4. Here the blood vessel 62 is shown in phantom as are the radio-translucent or radio-transparent elements of the balloon catheter 60 and the guidewire 20, e.g., the first coiled spring wire 28.

In an exaggerated manner, the increasing spacing of the coils 48 of the radiopaque second coiled spring wire 36 in a distal end portion 70 of the guidewire 20 as seen fluoroscopically is shown in FIG. 5.

As shown, the second coiled spring wire 36 is wound so as to have a short coiled section of small diameter, e.g. the at least one interior coil 44 and then quickly increases to a diameter which matches the diameter of the primary or first coiled spring wire 28. The larger diameter coils 48 of the second coiled spring wire are then interwound or interleaved with the coils 50 of the first coiled spring wire 28 as shown in FIG. 3 and the interleaved coils 48 and 50 are constructed and arranged so that the spacing S between the coils is very gradual, so as to create a gradual change in spring force to make it easier to "track" the vacsularture into which the guidewire 20 is inserted.

A primary advantage of the guidewire 20 is that only the most distal portion 70 of the guidewire 20 is visible under fluoroscopy, as shown in FIG. 5. This makes it easier to view the critical area of stenosis 64 being treated. Additionally, the gradual change in spacing S of the coils 48 and 50 in the distal portion 70 of the guidewire 20 allows a gradual transition to be created at the distal tip area 70 of the guidewire 20 so as to make it easier for the guidewire 20 to follow the vasculature into which it is inserted.

From the foregoing description, it will be apparent that the guidewire 20 having a controlled radiopacity tip of the present invention has a number of advantages, some of which have been described above, and others of which are inherent in the invention. Accordingly, the scope of the invention is only to be limited as necessitated by the accompanying claims.

We claim:

1. A controlled radiopaque guidewire comprising:

an elongate central core wire having a reduced in diameter distal end portion, a rounded tip member having a back side to which is connected a distal end of said core wire;

a first coiled spring wire having a proximal end fixed to said core wire in a proximal area thereof and a distal end fixed to said back side of said tip member;

the coils of said first coiled spring wire being stretched or spaced in a distal end portion thereof;

a second coiled spring wire having a proximal end fixed to said core wire and coiling outward therefrom to and between the spaced apart coils in said first coiled spring wire in said distal end portion of said first coiled spring wire and interleaved therebetween;

a distal end of said second coiled spring wire being fixed to said back side of said tip member;

said proximal end of said second coiled spring wire being spaced inwardly of and not in connection with coils of said first coiled spring wire such that said coils in said proximal end portion of said second coiled spring wire have a smaller diameter than said coils of said first coiled spring wire;

said second coiled spring wire being more radiopaque than said first coiled spring wire;

the spacing between the interleaved coils of said first and second coiled spring wires increasing gradually from the beginning of the interleaving to said tip member; and, at least one coil of said second coiled spring wire at said proximal end of said second coiled spring wire being wound tightly around a reduced in diameter portion of said central core wire and fixed to said core wire and not being welded or otherwise fixed to coils of said first coiled spring wire.

2. The guidewire of claim 1 wherein at least two coils of said second coiled spring wire at the proximal end of said second coiled spring wire are tightly wound around said central core wire at the beginning of a tapered area of said core wire and fixed thereto by brazing.

3. The guidewire of claim 2 wherein said second coiled spring wire has a least one coil that extends from the connection to said central core wire within coils of said first coiled spring wire and then to an interleaved position between coils of said first coiled spring wire.

4. The guidewire of claim 1 wherein the distal portion of said guidewire is tapered to a small diameter distal end which is fixed to said tip member.

5. The guidewire of claim 1 wherein said first coiled spring wire comprises non-radiopaque coils and said second coiled spring wire comprises radiopaque coils.

* * * * *